US007091869B2

United States Patent
Forster et al.

(10) Patent No.: US 7,091,869 B2
(45) Date of Patent: Aug. 15, 2006

(54) OPTOACOUSTIC MEASURING ARRANGEMENT AND USE THEREOF

(75) Inventors: Martin Forster, Jona (CH); Peter Nebiker, Zürich (CH)

(73) Assignee: Siemens Building Technologies AG, Zurich (CH)

( * ) Notice: Subject to any disclaimer, the term of this patent is extended or adjusted under 35 U.S.C. 154(b) by 359 days.

(21) Appl. No.: 10/148,949

(22) PCT Filed: Oct. 1, 2001

(86) PCT No.: PCT/CH01/00588

§ 371 (c)(1),
(2), (4) Date: Oct. 1, 2002

(87) PCT Pub. No.: WO02/31475

PCT Pub. Date: Apr. 18, 2002

(65) Prior Publication Data

US 2003/0112019 A1    Jun. 19, 2003

(30) Foreign Application Priority Data

Oct. 9, 2000 (EP) ................. 00121937
May 15, 2001 (CH) ................. 896/01

(51) Int. Cl.
*G08B 17/10* (2006.01)
(52) U.S. Cl. .............. 340/628; 340/630; 340/632; 340/577; 340/578; 340/581; 340/583; 340/584; 73/24.01; 73/24.02; 73/587
(58) Field of Classification Search .......... 340/628, 340/629, 630, 632, 577, 578, 583, 584, 581; 73/24.01, 24.02, 587, 601; 250/343, 344; 324/633, 670
See application file for complete search history.

(56) References Cited

U.S. PATENT DOCUMENTS

| | | | | | |
|---|---|---|---|---|---|
| 4,058,725 | A | * | 11/1977 | Aine | ............... 250/343 |
| 4,594,004 | A | | 6/1986 | Ishida et al. | ............. 356/433 |
| 4,740,086 | A | * | 4/1988 | Oehler et al. | ........... 356/432 |

(Continued)

FOREIGN PATENT DOCUMENTS

DE    1807613    7/1969

(Continued)

OTHER PUBLICATIONS

"Nutzung der Inharenten Sensorischen Eigenschaften von Piezoelektrischen Aktoren" by Klaus Kuhnen und Hartmut Janocha; *Technisches Messen*, vol. 66, 1999, pp. 132-138.

(Continued)

*Primary Examiner*—Hung Nguyen
(74) *Attorney, Agent, or Firm*—Baker Botts LLP

(57) ABSTRACT

The measuring arrangement contains a measuring cell and a reference cell, respectively, and microphones assigned to these cells, to which microphones an electronic evaluation circuit is connected and in which a subtraction of the signals of the microphones takes place, as well as a radiation source for applying a modulated signal to the measuring cell. The modulation frequency of the radiation source coincides with the resonant frequency of the measuring cell, and the measuring cell and the reference cell are open at at least one end to the gas to and/or aerosol to be detected. The measuring arrangement is used as smoke alarm, gas alarm, fire hazard alarm or as combined smoke and gas alarm, wherein each of the measuring cells is exposed to a radiation of a wavelength at which a relevant substance to be detected is absorbent and an opto-acoustic effect is produced as a result.

15 Claims, 1 Drawing Sheet

U.S. PATENT DOCUMENTS

| | | | |
|---|---|---|---|
| 4,817,413 A | 4/1989 | Asano et al. | 73/24 |
| 5,159,411 A * | 10/1992 | Hammerich et al. | 356/432 |
| 5,331,845 A * | 7/1994 | Bals et al. | 73/61.43 |
| 5,933,245 A * | 8/1999 | Wood et al. | 356/437 |
| 6,006,585 A | 12/1999 | Forster | 73/24.01 |

FOREIGN PATENT DOCUMENTS

| | | |
|---|---|---|
| DE | 4132110 | 4/1993 |
| DE | 19637614 | 11/1997 |
| DE | 19826629 | 12/1999 |
| EP | 0849576 | 12/1997 |

OTHER PUBLICATIONS

"Differential Helmholtz Resonator as an Optoacoustic Detector"; G. Busse and D. Herboeck; *Applied Optics*; vol. 18 No. 23, Dec. 1, 1979, pp. 3959-3961.

"Design of Optoacoustic Systems"; C. Forbest Dewey, Jr.; Massachusetts Institute of Technology; *Academic Press*, New York, 1977, pp. 47-77.

\* cited by examiner

OPTOACOUSTIC MEASURING ARRANGEMENT AND USE THEREOF

CROSS-REFERENCE TO RELATED APPLICATIONS

This is a national application for International Application No. PCT/CH01/00588 which was filed on Oct. 1, 2001 and which published in German on Apr. 18, 2002, which in turn claims priority from 00121937.7, which was filed on Oct. 9, 2000, and 896/01, which was filed on May 15, 2001, of which the following is a

SUBSTITUTE SPECIFICATION

1. Field of the Invention

The present invention relates to an opto-acoustic measuring arrangement for the detection of gases and/or aerosols. The arrangement includes a measuring cell and a reference cell, microphones, respectively, assigned to each cell, an electronic evaluation circuit connected to the microphones in which a subtraction of the signals of the microphones occurs, and a radiation source for applying a modulated signal to the measuring cell. The modulation frequency of the radiation source coincides with the resonant frequency of the measuring cell.

2. Background of the Invention

With an opto-acoustic or photo-acoustic effect, an acoustic pressure wave, magnitude of which is directly proportional to the concentration of the relevant gas, is produced by the irradiation by modulated light of a gas to be detected. The acoustic pressure wave is produced because the gas absorbs the light radiation and as a result heats up. This results in a thermal expansion and a periodic pressure fluctuation in accordance with the modulation of the light radiation. A measuring cell and a reference cell are used in conjunction with a measuring arrangement in which the cells are either separated from each other and the radiation passes through both cells (C. F. Dewey, Jr.: Opto-acoustic Spectroscopy and Detection, [Y. H. Pao, ed.], Academic Press, New, York, 1977, 47–77). Alternatively, the cells may be interconnected, where the radiation passing only through the measuring cell (G. Busse and D. Herboeck: Differential Helmholz resonator as an opto-acoustic detector, Applied Optics, Vol 18, No. 23, 3959).

In the detection of aerosols, the behavior is similar, since aerosols also absorb the modulated radiation, and a modulated heat and modulated pressure are produced as a result. Previously described opto-acoustic sensors for the measurement of aerosols are mostly mono-sensors with only one measuring cell. Where two cells (so-called dual sensors having one measuring cell and one reference cell), are called for, they are constructed so that the reference cell is screened against the aerosol by filtering the air before it reaches the reference cell. Also due to the severe temperature-dependence of the resonant frequency, it is necessary to correct the magnitude of the signal.

The detection sensitivity of opto-acoustic "dual" sensors for gases or aerosols is in the region of that of optical smoke alarms. Since the opto-acoustic signals are produced by absorption and not by radiation, both large and even the smallest aerosols are able to be detected to below the μ range in accordance with the opto-acoustic principle. Moreover, light and dark types of smoke are able to be measured, more or less to an equal degree. Nevertheless, the opto-acoustic principle has not been used for smoke detection, primarily because of the additional expense attributable to air filtering, and the correction of the signal magnitude.

SUMMARY OF THE INVENTION

These drawbacks are solved according to the present invention, namely an opto-acoustic measuring arrangement of the type described at the outset and wherein the measuring cell and the reference cell are open at least at one end to the gas and/or aerosol to be detected. This arrangement eliminates the need to filter the gas/aerosol being investigated. Normally the sensor signal is zero, and a signal which requires only a relatively simple electronic circuit for its processing is produced in the measuring cell, and then only in the presence of aerosol or a combustible gas which absorbs the radiation emitted by the radiation source.

In a preferred embodiment of the present invention the electronic evaluation circuit contains a differential amplifier and a phase-sensitive rectifier.

In another preferred embodiment of the novel measuring arrangement the wavelength of the radiation emitted by the radiation source is chosen so that it is absorbed by the gas to be detected. In this case, a first photocell for monitoring the intensity of the radiation emitted by the radiation source is preferably disposed within the range of the radiation source.

In yet another preferred embodiment of the measuring arrangement according to the present invention, a second photocell is provided in addition to the measuring cell, which in the presence of an aerosol is exposed to the scattered radiation of the radiation source caused by the aerosol. A measuring arrangement constructed in this manner can detect both an aerosol, e.g. smoke, and a gas, and is therefore eminently suitable for use as a so-called dual-criteria alarm for smoke and gas. In practice, a specific aerosol is absorbed at a specific wavelength range, depending on the type of aerosol emitted by the combustible material. However, since the smoke from a fire nearly always contains mixtures of organic substances, e.g. wood, which are highly absorbent in the entire infrared range and still sufficiently absorbent in the visible light range, the choice of wavelength for optimum aerosol detection is generally not critical. If only smoke is to be detected, the second photocell is not required because in this case a wavelength can be selected at which no combustible gases are absorbed. In the detection of smoke and gas, the second photocell is generally always required when the gas to be detected has an absorption range similar to the aerosol.

In another preferred embodiment of the present invention the measuring cell is radiated by two radiation sources which are operated at different frequencies. This arrangement is suitable for the detection of smoke and two gases.

In a further preferred embodiment of the measuring arrangement according to the present invention, two pairs of measuring cells and reference cells, open at both ends, are provided, each of which has a different length and thus different resonant frequencies. Further, a microphone is assigned to each reference cell pair and to each measuring cell pair, and each measuring cell is exposed to a radiation source. The measuring arrangement having the two pairs of measuring cells and reference cells is suitable for the detection of smoke and two gases. By adding a further pair with a measuring cell and a reference cell, the detection range of the measuring arrangement can be extended to a third gas.

The present invention further includes a smoke alarm application for the novel measuring arrangement. Here the measuring arrangement has a measuring cell which is exposed to radiation having a wavelength at which the aerosol to be detected is absorbed, and as a result, an opto-acoustic effect is produced.

A fire hazard alarm is another application for the measuring arrangement of the present invention. Here the measuring arrangement has a measuring cell which is exposed to radiation having a wavelength at which a combustible or explosive substance to be detected is absorbed, and as a result, an opto-acoustic effect is produced.

The invention further includes a combined smoke and gas alarm application for the novel measuring arrangement. Here the measuring arrangement has a measuring cell which is exposed to radiation having a wavelength at which a combustible or explosive substance to be detected is absorbed, and as a result, an opto-acoustic effect is produced. Furthermore, in addition to the measuring cell, a photocell is provided so that it is exposed to scattered light of the radiation caused by an aerosol.

A combined fire alarm and fire hazard alarm is another application of the novel measuring arrangement. Here the measuring arrangement has two measuring cells, one of which is exposed to radiation having a wavelength at which the aerosol or a combustible gas to be detected is absorbed, and the other of which is exposed to radiation having a wavelength at which a combustible or explosive substance to be detected is absorbed, and as a result, an opto-acoustic effect is produced.

BRIEF DESCRIPTION OF THE DRAWINGS

The present invention is described hereinbelow in greater detail in conjunction with exemplary embodiments, and drawings, in which.

DETAILED DESCRIPTION OF THE INVENTION

Figure 1:
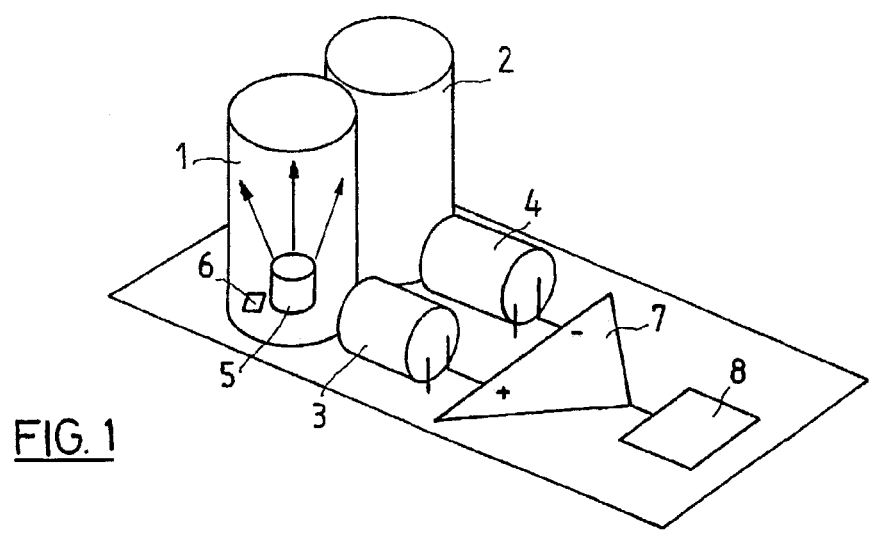
FIG. 1 illustrates a schematic representation of a resonant, opto-acoustic dual sensor, open at one end for smoke and gas.

The opto-acoustic measuring arrangement illustrated in FIG. 1 is a resonant, dual sensor, open at one end, with a tubular measuring cell 1 and a tubular reference cell 2, to each of which a microphone 3 and 4, respectively, is assigned. Furthermore, a radiation source 5, for example an LED, is provided, which exposes the inner space of the measuring cell 1 with radiation of a specific wavelength. In addition to the radiation source 5, a first photocell 6 is disposed for monitoring the intensity of the radiation emitted by the radiation source 5. The outputs of the two microphones 3 and 4 are fed to a differential amplifier 7 in which the microphone signals are subtracted from each other. The output signal of the differential amplifier 7 is fed to a phase-sensitive rectifier (lock-in) 8.

Tubes open at one end, with a length "l" have a resonant frequency Vk, which is given by the formulae:

$$vk = \frac{2k+1}{4l} c,$$

where (k=0,1,2,3, . . . ; c=velocity of sound air)

With a length 1 of 2 cm, this gives a resonant frequency $v_o$=4.1 kHz; with a tube open at both ends this resonant frequency is doubled. Standing waves therefore occur in the tube, wherein in the case of the tube open at one end, a pressure antinode (=motion node) occurs at the closed end, and a pressure node (=motion antinode) occurs at the open end. In the tube open at both ends, the pressure antinode is located at the center of the tube, and a motion antinode at each open end.

The radiation source 5 emits modulated radiation into the measuring cell 1, the modulation frequency of the radiation source 5 coinciding with the resonant frequency of the measuring cell. If the measuring cell 1 contains an aerosol, then this absorbs the modulated radiation, thereby producing modulated heat. The modulated heat produces modulated pressure and thus sound at the frequency of the resonant frequency of the measuring cell 1, as a result of which the air column in the measuring cell is excited into oscillation. The same applies in the presence of a gas in the measuring cell 1. The microphone 3, which is located at the position of a pressure antinode of the standing wave, measures the oscillations (=sound) in the tube. As soon as the microphone 3 measures a sound which coincides with the resonant frequency of the measuring cell 1, there is an aerosol and/or a gas in the measuring cell 1.

In contrast to a scattered-light smoke alarm, the measuring arrangement according to FIG. 1 responds equally well to dark and light aerosols. Dark aerosols produce a large signal because when the radiation of the radiation source 5 initially strikes a particle, a large amount of radiation power is absorbed. Light aerosols also produce a large signal, since the radiation striking the light particles is reflected many times and in total is absorbed to a great extent. Moreover, the opto-acoustic sensor responds both to large aerosols, as well as to very small ones (below the µ range), since the opto-acoustic signals are generated by absorption and not by scattering.

The microphone 3 measures not only the resonant oscillations in the measuring cell 1, but also all noises in the room, which can lead to interference. This interference is eliminated by the reference cell 2 and the microphone 4. Since the reference cell 2 is not exposed to the radiation of a radiation source, the microphone 4 also cannot measure any oscillations produced by a radiation source, but exclusively measures the noise in the room. The signals of the reference microphone 4 are subtracted in the differential amplifier 8 from the signals of the measuring microphone 3, thus eliminating the room noise. Vibrations, which have an equal effect on both microphones, are likewise eliminated. The two cells, measuring cell and reference cell, can also be open at both ends.

Figure 2:
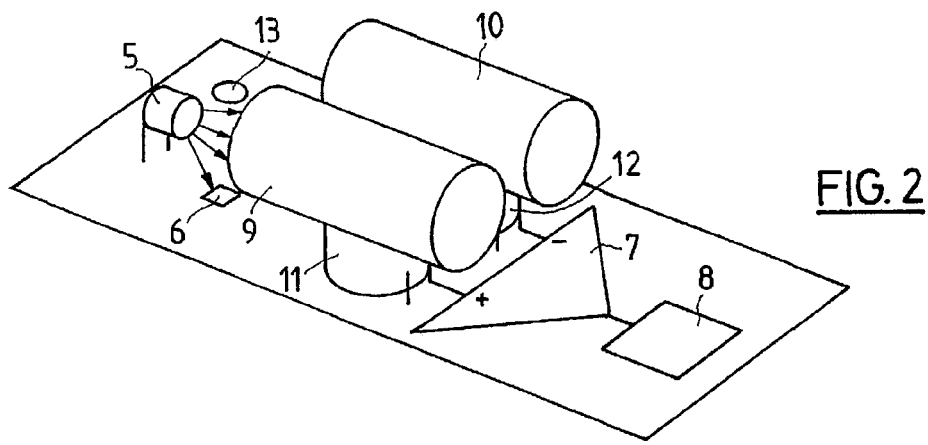
FIG. 2 illustrates a schematic representation of a resonant, opto-acoustic dual sensor, open at both ends for smoke and gas.

FIG. 2 illustrates an arrangement with a measuring cell 9, open at both ends, a reference cell 10, open at both ends, a measuring microphone 11 and a reference microphone 12. A second photocell 13, which is disposed in the region between the radiation source 5 and the measuring cell 1, is also shown in FIG. 2. The position of the second photocell 13 is chosen so that in the presence of particles in the area between radiation source 5 and measuring cell 1, a portion of the scattered light of the radiation of the radiation source 5 produced by these particles falls on the photocell 13. The second photocell 13 enables a distinction to be made between aerosol and gas. If both the measuring cell 1 and the second photocell 13 deliver a signal, then an aerosol is present. If only the measuring cell 1 delivers a signal, then either a gas or a very small, and therefore non-scattering aerosol is present.

If the suppression of room noise and vibrations can be dispensed with, in principle a measuring arrangement without reference cell 2 and the microphone 4 assigned to the former would be adequate. If in such an arrangement the wavelength of the radiation source 5 is placed on the $CO_2$ line, then the measuring arrangement will measure very sensitively the concentration of the combustion gas $CO_2$ on the one hand and the concentration of aerosol on the other.

The measuring arrangements illustrated in FIGS. 1 and 2 can be designed as a gas alarm, smoke (aerosol) alarm, a combined gas and smoke alarm, and it can be used in these various forms as a fire alarm or as a fire hazard alarm. A fire alarm detects smoke and/or combustion gases, or generally substances which characterize a fire. A fire hazard alarm detects, on the one hand, an existing fire by detecting an aerosol or substances occurring in a fire, and on the other hand it detects toxic substances occurring in a fire, and recognizes the danger of a possible fire or a possible explosion by detecting the presence of combustible substance in the air.

Substances which characterize a fire are, in particular, the following: $CO_2$, $CO$, $NO$, $NO_2$, $SO_2$, $NH_3$, $HCI$, $HF$, $HCN$, amine and amide, compounds containing hydrocarbons, C, O and H; aerosols. Combustible substances are generally hydrocarbons, particularly $CH_4$, $C_2H_6$, $C_3H_8$, $C_4H_{10}$, $C_2H_2$, $C_2H_4$, as well as general solvents, alcohol, ether, ketone, aldehyde, amine and amide, in particular methanol, ethanol, n-propanol, diethylether, acetone. Other combustible substances which a fire hazard alarm should detect are compounds containing C, O, H, and carboxylic acids. Toxic substance are $CO_2$, $CO$, $NO$, $NO_2$, $SO_2$, $NH_3$, $HCI$, $HF$, $HCN$, $H_2S$, nitrites, phosphoric ester, mercaptans, halogenated compounds.

Since the velocity of sound in air is temperature-dependent and can vary by up to 30% in the temperature range of a fire alarm from $-20°$ C. to $+70°$ C., the resonant frequency can also change accordingly. Water vapor also influences the velocity of sound and thus the resonant frequency. In order to eliminate these influences, the rough range of the resonant frequency and the possible additional expansion of the frequency range by varying water vapor content in the air, can be calculated with a temperature measurement and the modulation frequency of the radiation source varied (swept) in this range.

A further possible disturbance consists in frequencies in the room, which coincide with the resonant frequency. Such frequencies excite both cells into oscillation, but cannot be completely subtracted to zero by the differential circuit, because, due to the distance from the center of the measuring cell 1, 9 to the center of the reference cell 2, 10, they strike the cells with a time shift and excite these cells into oscillation which has a small phase shift. This phase shift can be minimized by a lowest possible resonant frequency, because the interfering audio frequencies then have a large acoustic wavelength and the phase shift becomes small. Alternatively, the signal of the reference cell 2, 10 can be measured separately, and when a signal, (which in fact can be generated only from outside) impinges upon the reference cell, the alarm threshold of the measuring arrangement can be increased.

Further potential disturbance variables are different lengths of the cells. These disturbance variables can be eliminated by measuring the resonant frequency of one of the two cells and mechanically varying the length of the other cell accordingly. The resonant frequency of the reference cell can also be measured and the radiation source 5 positioned so that its position influences the resonant frequency of the measuring cell and brings it into coincidence with the reference cell.

As a further check, monitoring of the microphone sensitivity by means of the zero signals produced by the radiation source in the wall of the measuring cell 1, 9, which occur under all environmental conditions, is recommended.

Figure 3:
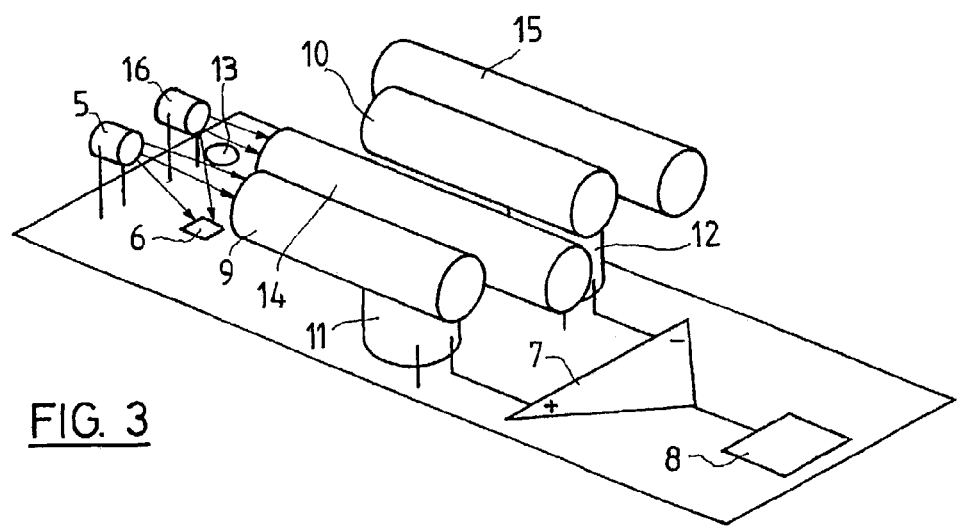
FIG. 3 illustrates another embodiment of the dual sensor of FIG. 2.

The arrangement illustrated in FIGS. 1 and 2 for the measurement/detection of smoke and one gas can be expanded by an additional pair of cells for the measurement/detection of a further gas. According to FIG. 3, an additional measuring cell 14, an additional reference cell 15 and an additional radiation source 16 are provided, where the measuring cell 9 measures aerosol and a first gas, and the measuring cell 14 measures a second gas, for example. The two measuring cells 9 and 14 and, correspondingly, also the two reference to cells 10 and 15 have different lengths and therefore also different resonant frequencies. The two measuring cells are exposed to radiation from the radiation sources 5 and 16, respectively, at different wavelengths. The two different resonant frequencies can be measured with just one measuring microphone 11. Likewise, only one reference microphone 12, and only one single photocell 6 are required for monitoring the emission of both radiation sources 5 and 16.

The measuring cells and reference cells can have the following dimensions, for example: measuring cell 9, reference cell 10 each 2 cm in length, and each has a resonant frequency of 8.2 kHz; measuring cell 14, reference cell 15: each 2.2 cm in length, and each has a resonant frequency of 7.6 kHz. Accordingly, the modulation frequency of the radiation source 5 is 8.2 kHz, and that of the radiation source 16 is 7.6 kHz. LEDs are used as radiation sources.

Accordingly, the added expense for the detection of a second gas is only the cost of the second cell pair, and for the second radiation source. It is quite obvious that an extension for the detection of a third gas requires only a further cell pair and a further radiation source.

Instead of two pairs of measuring and reference cells (9, 10; 14, 15), of different length, which are simultaneously irradiated by two radiation sources 5 and 16, in the arrangement of FIG. 2 the measuring cell 9 of one cell pair can be simultaneously irradiated by two radiation sources 5 and 16 and these can be operated at difference frequencies; for example, the radiation source 5 at the fundamental frequency and the radiation source 16 at the first harmonic. Consequently, compared to the arrangement of FIG. 3, only half the number of cells and microphones are needed and corresponding costs are saved.

Apart from the resonant opto-acoustic dual sensors, open at one end or both ends, non-resonant, closed dual sensors are also known (see for example EP-A-0 855 592), which can likewise be constructed so that the detection of aerosols and gases is possible with them. As can be seen in EP-A-0 855 592, these opto-acoustic dual sensors contain a measuring cell and a reference cell, each of which is sealed against the environment by a diaphragm, and a radiation source. Gas can permeate the cell through the diaphragm. A measuring microphone and a reference microphone are provided, the reference microphone being screened against opto-acoustic signals of the gas/aerosol to be detected. So that aerosol particles can permeate the cells, the pore size of the diaphragms is increased accordingly.

However, as a result, the diaphragms for frequencies below 500 Hz are acoustically soft. Accordingly, pressure build-up in the cell is no longer possible, and the sensitivity is seriously reduced. By increasing the modulation frequency by a few kilohertz, the diaphragms again become acoustically hard, and the sensitivity no longer decreases. Any jamming of the diaphragms can be monitored by measuring the reference signal separately, which gives a base noise level, and the sensitivity corrected with the aid of this base level. If the wavelength of the radiation sources is positioned on the $CO_2$ line, for example, then the measuring arrangement will measure very sensitively the concentration of the $CO_2$ combustion gas. On the other hand, however, the concentration of aerosol is very sensitively measured because cellulose and carbonized cellulose particles are strongly absorbent in the entire infrared range. The volume per cell is approximately 2 times 2 times 2 cm$^3$.

The invention claimed is:

1. An opto-acoustic measuring arrangement for detecting a gas and/or an aerosol, comprising a measuring cell, a reference cell open at at least one end to the gas and/or aerosol to be detected, a microphone associated with each of said cells and connected to an electronic evaluation circuit in which a subtraction of signals of the microphones occurs, and further comprising a radiation source for applying a modulated signal to the measuring cell, wherein a modulation frequency of the radiation source coincides with a resonant frequency of the measuring cell and the reference cell is only exposed to the gas and/or aerosol to be detected.

2. The measuring arrangement according to claim 1, wherein the electronic evaluation circuit contains a differential amplifier and a phase-sensitive rectifier.

3. The measuring arrangement according to claim 1, wherein the radiation source emits a wavelength of radiation chosen so that it is absorbed by the gas to be detected.

4. The measuring arrangement according to claim 3, further comprising a first photocell for monitoring an intensity of the radiation emitted by the radiation source, disposed in a region of the radiation source.

5. The measuring arrangement according to claim 4, further comprising a second photocell which, in a presence of an aerosol, is exposed to scattered radiation of the radiation source caused by the aerosol.

6. The measuring arrangement according to claim 1, wherein the measuring cell is exposed to two radiation sources, which are operated at different frequencies.

7. The measuring arrangement according to claim 6, wherein one of the radiation sources is operated at a fundamental frequency and another is operated at a first harmonic.

8. The measuring arrangement according to claim 1, further comprising two pairs of measuring cells and reference cells, open at both ends, wherein each has a different length and thus different resonant frequencies, the microphone is associated with each reference cell, and each measuring cell pair, wherein each measuring cell is exposed to the radiation source.

9. The measuring arrangement according to claim 8, further comprising a sensor for measuring ambient temperature, and wherein an adjustment is made to the modulation frequency of the radiation source to a frequency range corresponding to the measured ambient temperature, and a time-shift of the modulation frequency within the frequency range.

10. The measuring arrangement according to claim 1, for use as a smoke alarm, wherein the measuring arrangement has a measuring cell, which is exposed to a radiation of a wavelength at which the aerosol to be detected is absorbed, and an opto-acoustic effect is produced as a result.

11. The measuring arrangement according to claim 1, for use as a fire hazard alarm, wherein the measuring arrangement has a measuring cell, which is exposed to a radiation of a wavelength at which a combustible or explosive substance to be detected is absorbed, and an opto-acoustic effect is produced as a result.

12. The measuring arrangement according to claim 11, wherein the combustible or explosive substance to be detected is formed by at least one substance selected from the group consisting of hydrocarbons, including $CH_4$, $C_2H_6$, $C_3H_8$, $C_4H_{10}$, $C_2H_2$, $C_2H_4$, as well as general solvents, alcohol, ether, ketone, aldehyde, amine and amide, methanol, ethanol, n-propanol, diethylether, acetone, compounds containing C, O and H, and carboxylic acids.

13. The measuring arrangement according to claim 11, wherein the measuring arrangement has a measuring cell, which is exposed to the radiation of a wavelength at which a toxic substance to be detected is absorbed, and an opto-acoustic effect is produced as a result.

14. The measuring arrangement according to claim 13, wherein the toxic substance to be detected is formed by at least one of the following substances: $CO_2$, CO, NO, $NO_2$, $SO_2$, $NH_3$, HCI, HF, HCN, $H_2S$, nitrites, phosphoric ester, mercaptan, halogenated compounds.

15. The measuring arrangement according to claim 1, for use as a combined smoke and gas alarm, wherein the measuring arrangement has the measuring cell, which is exposed to a radiation of a wavelength at which a combustible or explosive substance to be detected is absorbed, and an opto-acoustic effect is produced as a result, and that in addition to the measuring cell, a photocell is provided so that it is exposed to scattered light of the radiation caused by the aerosol.

* * * * *